(12) United States Patent
Ko et al.

(10) Patent No.: US 9,743,895 B2
(45) Date of Patent: Aug. 29, 2017

(54) MAMMOGRAPHY APPARATUS

(71) Applicant: SAMSUNG ELECTRONICS CO., LTD., Suwon-si, Gyeonggi-do (KR)

(72) Inventors: Su Young Ko, Hwaseong-si (KR); Woo Sup Han, Yongin-si (KR); Hyung Won Yoon, Seoul (KR); Jin Ho Choi, Anyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 256 days.

(21) Appl. No.: 14/563,332

(22) Filed: Dec. 8, 2014

(65) Prior Publication Data
US 2015/0164449 A1 Jun. 18, 2015

(30) Foreign Application Priority Data
Dec. 17, 2013 (KR) ........................ 10-2013-0157266

(51) Int. Cl.
*A61B 6/00* (2006.01)

(52) U.S. Cl.
CPC ............ *A61B 6/4488* (2013.01); *A61B 6/502* (2013.01)

(58) Field of Classification Search
CPC ......... A61B 6/502; A61B 6/0414; A61B 6/04; A61B 6/0435; A61B 8/0825; G06T 2207/30068; G06T 2207/10116
See application file for complete search history.

(56) References Cited

U.S. PATENT DOCUMENTS

| 7,729,470 B2 | 6/2010 | Fischer et al. | |
| 2008/0247508 A1* | 10/2008 | Harrington | A61B 6/0414 378/37 |
| 2009/0086890 A1* | 4/2009 | Hakamata | A61B 6/4233 378/37 |

FOREIGN PATENT DOCUMENTS

JP 2005-349207 12/2005

* cited by examiner

*Primary Examiner* — Hoon Song
(74) *Attorney, Agent, or Firm* — Staas & Halsey LLP

(57) ABSTRACT

A mammography apparatus minimizes the displeasure experienced by a human during x-ray operations, the displeasure being generated by a low temperature of a portion of the mammography apparatus making contact with the human body. The displeasure is minimized by increasing and maintaining the temperature of the portion of the mammography apparatus. The mammography apparatus includes an x-ray generating unit to generate x-rays, and an x-ray detecting unit having a detector to obtain x-ray data by detecting the x-ray passing through a subject. The x-ray detecting unit includes a housing forming an outer appearance of the x-ray detecting unit, a thermoelectric element provided at an inside the housing, and is disposed such that a cooling unit faces a lower surface of the detector, and a heat pipe extends to an inner side surface of the housing from a heat generating unit of the thermoelectric element.

21 Claims, 6 Drawing Sheets

MAMMOGRAPHY APPARATUS

CROSS-REFERENCE TO RELATED APPLICATIONS

This application claims the priority benefit of the Korean Patent Application No. 10-2013-0157266, filed on Dec. 17, 2013, in the Korean Intellectual Property Office, the disclosure of which is incorporated herein by reference.

BACKGROUND

1. Field

Embodiments disclosed herein relate to an x-ray photographic apparatus (e.g., a mammography apparatus) which may be used to photograph (obtain an image of) an object (e.g., breasts) by use of x-rays.

2. Description of the Related Art

An x-ray photographic apparatus generally refers to a device used to obtain an image of an inside of a subject by use of an x-ray. The x-ray photographic apparatus may be able to generate an image of an inside of a subject in a non-invasive method by radiating an x-ray to the subject and then by detecting the x-ray that is penetrated through the subject. The x-ray photographic apparatus, which may be employed or utilized for a medical purpose, may be used to diagnose an injury or a disease inside of a subject that is not easily identified from the outside of the subject.

A mammography apparatus is an example apparatus among the x-ray photographic apparatuses which is used to photograph breasts of a human (a female) by use of an x-ray. A doctor or other medical professional may be able to diagnose a possibility of an occurrence of breast cancer by observing the image that is photographed.

The mammography apparatus may be used to obtain an image by radiating an x-ray to breasts after compressing bodily tissues inside the breasts. The mammography apparatus may include a pressing paddle which may be used to compress the breasts and an x-ray detecting unit.

SUMMARY

Therefore, it is an aspect of the disclosure to provide a mammography apparatus for increasing and maintaining the temperature of a portion of the mammography apparatus making contact with a body.

Additional aspects of the disclosure will be set forth in part in the description which follows and, in part, will be apparent from the description, or may be learned by practice of the disclosure.

In accordance with an aspect of the disclosure, a mammography apparatus may include an x-ray generating unit and an x-ray detecting unit. The x-ray generating unit may be configured to (suitable for, adapted to, capable of, arranged to, operable to, etc.) generate x-rays. The x-ray detecting unit may have a detector configured to (suitable for, adapted to, capable of, arranged to, operable to, etc.) obtain x-ray data by detecting the x-ray passing through a subject. The x-ray detecting unit may include a housing, a thermoelectric element and a heat pipe. The housing may form an outer appearance of the x-ray detecting unit. The thermoelectric element may be provided at an inside the housing, and disposed such that a cooling unit faces a lower surface of the detector. The heat pipe may be extended to an inner side surface of the housing from a heat generating unit of the thermoelectric element.

The heat pipe may be extended along an edge of one surface of the housing, the one surface being in contact with a subject.

The x-ray detecting unit may further include a heat insulating unit provided at an inside the housing and configured to (suitable for, adapted to, capable of, arranged to, operable to, etc.) insulate the heat pipe from other portions of the inside the housing.

The x-ray detecting unit may be provided with a temperature detecting sensor configured to (suitable for, adapted to, capable of, arranged to, operable to, etc.) detect the temperature of one surface of the housing being in contact with respect to a subject.

In a case when the temperature detected by the temperature detecting sensor is equal to or higher than a predetermined temperature, a current that flows at the thermoelectric element may be blocked, and in a case when the temperature detected by the temperature detecting sensor is lower than the predetermined temperature, current may flow at the thermoelectric element.

The thermoelectric element may be provided with metallic material having high heat conductivity.

A side of the cooling unit of the thermoelectric element may be blocked from a side of the heat generating unit by a blocking unit.

A thermal conductor may be provided at a lower surface of the detector.

The x-ray detecting unit may further include a heat pipe configured to (suitable for, adapted to, capable of, arranged to, operable to, etc.) connect the thermal conductor to the cooling unit of the thermoelectric element.

The thermal conductor may be provided at a side of a heat generating member provided at the detector.

In accordance with an aspect of the disclosure, a mammography apparatus may include an x-ray generating unit, a detector, a housing, a thermoelectric element, a heat pipe and a temperature detecting sensor. The x-ray generating unit may be configured to (suitable for, adapted to, capable of, arranged to, operable to, etc.) radiate x-rays to a subject. The detector may be configured to (suitable for, adapted to, capable of, arranged to, operable to, etc.) obtain an internal image of a subject by detecting the x-rays. The housing may be configured to (suitable for, adapted to, capable of, arranged to, operable to, etc.) accommodate the detector and at an upper surface of which the subject is positioned. The thermoelectric element may be accommodated at an inside the housing and have a heat generating unit and a cooling unit. The heat pipe may be extended from the heat generating unit to an inner side surface of the housing. The temperature detecting sensor may be configured to (suitable for, adapted to, capable of, arranged to, operable to, etc.) detect the temperature of the housing.

The temperature detecting sensor may be provided at a surface of the housing which is in contact with a subject.

The housing may further include a heat insulating unit configured to (suitable for, adapted to, capable of, arranged to, operable to, etc.) insulate the heat pipe.

The housing may further include a blocking unit configured to (suitable for, adapted to, capable of, arranged to, operable to, etc.) block a side of the cooling unit of the thermoelectric element from a side of the heat generating unit.

A thermal conductor may be provided at a lower surface of the detector.

The housing may further include a heat pipe configured to (suitable for, adapted to, capable of, arranged to, operable to, etc.) connect the cooling unit of the thermoelectric element to the thermal conductor.

The thermal conductor may be provided at a surface of the detector on which a heat generating member is positioned.

In accordance with an aspect of the disclosure, a method of controlling a temperature of a housing of an x-ray detecting unit in a mammography apparatus, may include: radiating, using an x-ray generator, x-rays to a subject, obtaining, using a detector disposed in the housing, an internal image of the subject by detecting the x-rays, cooling the detector using a cooler disposed in the housing below the detector, measuring, using one or more sensors, a temperature of the housing, comparing the measured temperature with a prestored temperature range, and controlling a heat generator disposed in the housing below the cooler, to selectively be turned on or off to control a temperature of the housing, based on the comparing.

For example, when the comparing indicates the measured temperature exceeds the prestored temperature range, the controlling may include turning off the heat generator, and when the comparing indicates the measured temperature is less than the prestored temperature range, the controlling may include turning on the heat generator.

The one or more temperature detecting sensors may be provided on at least one surface of the housing. The heat generator may be connected to a heat pipe which extends from the heat generator to an inner side surface of the housing. The heat pipe may further extend from the inner side surface of the housing to an inner top surface of the housing adjacent to a top surface of the housing upon which the subject is disposed.

As is apparent from the above, a mammography apparatus in accordance with one or more embodiments of the disclosure may be capable of minimizing the displeasure experienced by a subject when an x-ray of a breast is obtained, which is generated by a lower temperature of a portion of the mammography apparatus at which a portion of a body being in contact with respect to the portion of the mammography apparatus. The displeasure may be reduced, for example, by increasing and maintaining the temperature of the portion of the mammography apparatus which contacts the body part of the subject.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
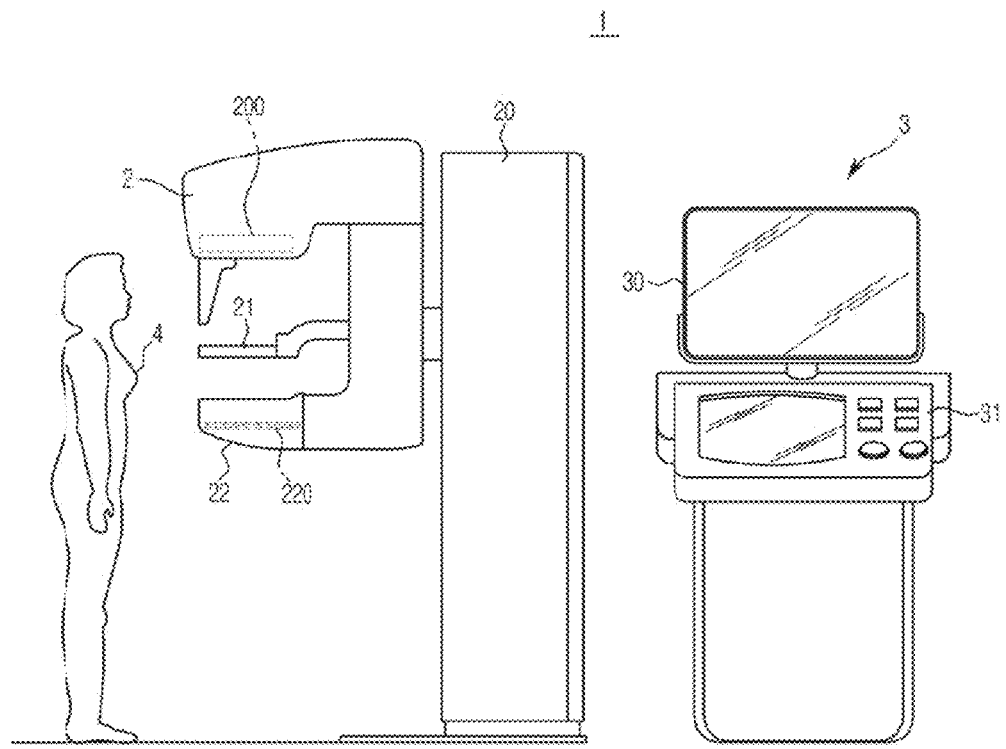
FIG. 1 is a drawing illustrating a mammography apparatus in accordance with an embodiment of the disclosure.

Reference will now be made in detail to the embodiments of the disclosure, the examples of which are illustrated in the accompanying drawings, wherein like reference numerals refer to like elements throughout.

Figure 2:
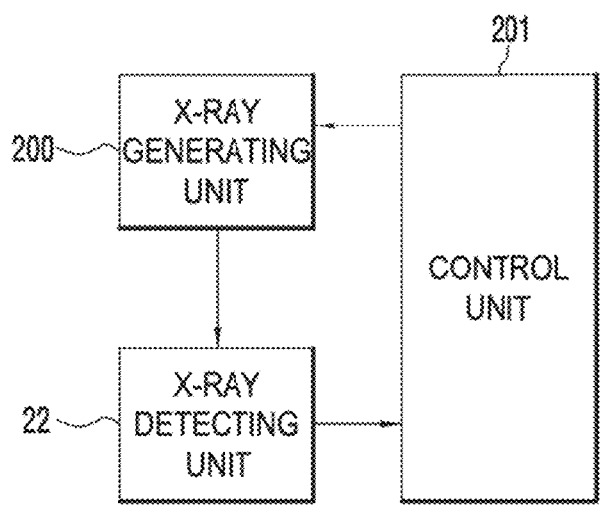
FIG. 2 is a control block diagram of the mammography apparatus in accordance with an embodiment of the disclosure.

FIG. 1 is a drawing illustrating a mammography apparatus in accordance with an embodiment of the disclosure, and FIG. 2 is a control block diagram of the mammography apparatus in accordance with an embodiment of the disclosure.

Referring to FIG. 1 and FIG. 2, a mammography apparatus 1 in accordance with an embodiment of the disclosure may include a body 2 and a host apparatus 3. An x-ray photographing or imaging may be performed by the body 2 on a specific area of a subject where a diagnosis is needed. Since the mammography apparatus 1 in accordance with an embodiment of the disclosure is designed to obtain an image of an inside of one or more breasts of a patient or subject by use of x-rays, hereinafter, the breasts may be referred to as a subject 4 of the mammography apparatus 1.

The host apparatus 3 may be able to input various commands with respect to an x-ray photographing into the body 2. X-ray data delivered from the body 2 by the host apparatus 3 may be generated as an x-ray image and displayed. The host apparatus 3 and the body 2 may be connected with one another over a wired or wireless network or a combination thereof.

The body 2 may include an x-ray generating unit 200, a control unit 201, a pressing paddle 21, and an x-ray detecting unit 22. At an upper portion of the body 2, the x-ray generating unit 200 may be positioned. At a lower portion of the body 2, the x-ray detecting unit 22 may be positioned. The pressing paddle 21 may be positioned in between the x-ray generating unit 200 and the x-ray detecting unit 22.

The x-ray generating unit 200 may be able to generate x-rays and radiate the generated x-rays to the subject 4. The x-ray detecting unit 22 may include a detector 220. The detector 220 may be able to obtain x-ray data by detecting x-rays penetrated through the subject 4 and then converting the detected x-rays into electric signals. The control unit 201 may be able to correct an image, for example, by pre-storing a calibration function that may be configured to (suitable for, adapted to, capable of, arranged to, operable to, etc.) calibrate an error caused by the characteristic of each pixel and then by applying the pre-stored calibration function on the x-ray data obtained at the time of photographing the subject 4.

The x-ray generating unit 200 may be configured to (suitable for, adapted to, capable of, arranged to, operable to, etc.) generate x-rays and radiate the x-rays to the subject 4. When the subject 4 corresponds to a subject's breasts, which are composed of soft tissues, a vertical compression may be needed to obtain a clearer and more accurate image of the subject 4 (e.g., breast). Thus, x-rays may be radiated by placing the subject 4 between the pressing paddle 21 and compressing the subject 4 using the pressing paddle 21. The x-ray generating unit 200, the x-ray detecting unit 22, and the pressing paddle 21 may be supported by a body housing 20 (e.g., a gantry).

The host apparatus 3 may include a display unit 30 and an input unit 31. The display unit 30 may be able to display the generated x-ray image. An operator may be able to input various commands with respect to operation of the mammography apparatus 1 through the input unit 31.

The display unit may include one or more of a liquid crystal display (LCD), a light emitting diode (LED) display, an organic light emitting diode (OLED) display, active matrix organic light emitting diode (AMOLED), flexible display, 3D display, a plasma display panel (PDP), a cathode ray tube (CRT) display, and the like, for example. The display unit may include a touch screen, and/or may be combined with an input device as a single device (e.g., a smart phone, tablet, etc.) However, the disclosure is not limited to these example displays and may include other types of displays.

The input unit may include, for example, one or more of a keyboard, a mouse, a joystick, a button, a switch, an electronic pen or stylus, a gesture recognition sensor (e.g., to recognize gestures of a user including movements of a body part), an input sound device or voice recognition sensor (e.g., a microphone to receive a voice command), an output sound device (e.g., a speaker), a track ball, a remote controller, a portable (e.g., a cellular or smart) phone, a tablet PC, a pedal or footswitch, a virtual-reality device, and so on. The input unit may further include a haptic device to provide haptic feedback to a user. The input unit may also include a touchscreen, for example.

Figure 3:
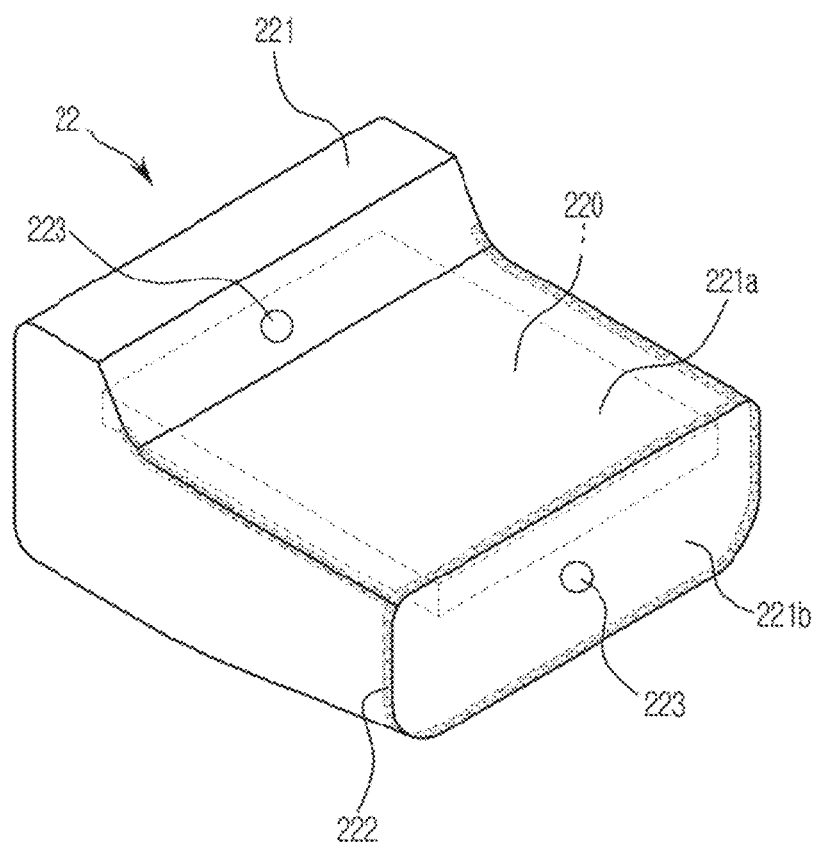
FIG. 3 is a drawing illustrating an x-ray detecting unit of the mammography apparatus in accordance with an embodiment of the disclosure.
Figure 4:
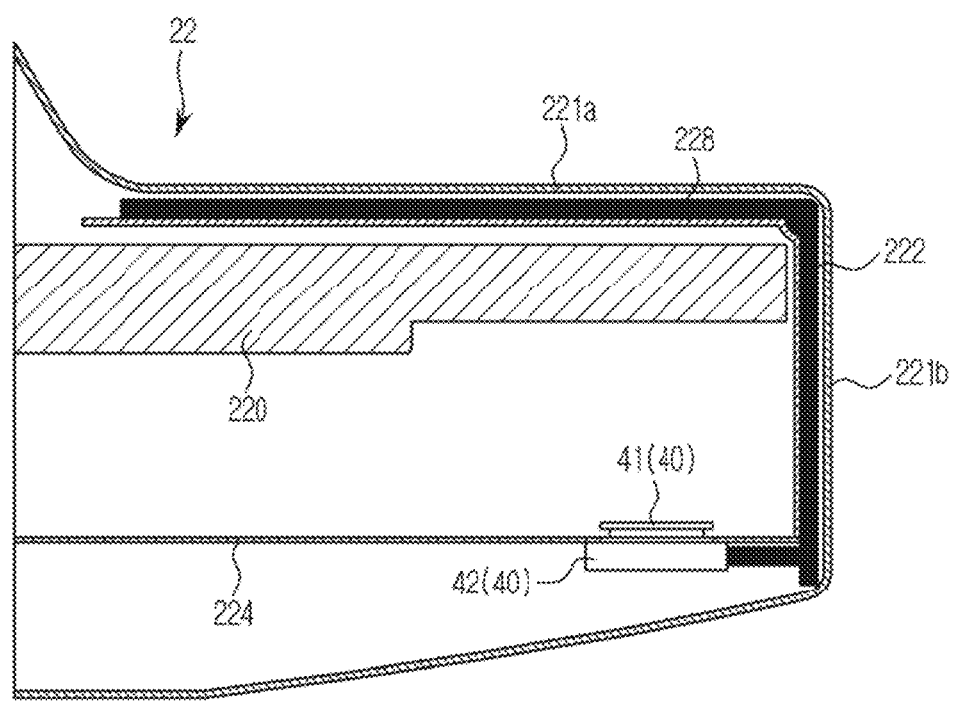
FIG. 4 is a cross-sectional view illustrating a portion of the x-ray detecting unit in accordance with an embodiment of the disclosure.

FIG. 3 is a drawing illustrating the x-ray detecting unit of the mammography apparatus in accordance with an embodiment of the disclosure, and FIG. 4 is a cross-sectional view illustrating a portion of the x-ray detecting unit in accordance with an embodiment of the disclosure.

Referring to FIG. 3 and FIG. 4, the x-ray detecting unit 22 of the mammography apparatus 1 in accordance with an embodiment of the disclosure may include a housing 221 forming an exterior appearance of the x-ray detecting unit 22, the detector 220 configured to (suitable for, adapted to, capable of, arranged to, operable to, etc.) detect x-rays radiated to the subject 4, and a thermoelectric element 40 having a cooling unit 41 and a heat generating unit 42. The detector 220 and the thermoelectric element 40 may be accommodated in the housing 221. The x-ray detecting unit 22 may further include a heat pipe 222. For example, the heat pipe 222 may be formed of metal having a high heat conductivity.

A surface of the housing 221 at which the subject 4 is positioned at the time of performing an x-ray photographing may be referred to as a first surface 221a. The first surface 221a may be an upper surface of the housing 221. The other surface coming into contact with a human body when the subject 4 is positioned on the first surface 221a may be referred to as a second surface 221b. The second surface 221b and the first surface 221a may share at least one edge. For example, the first surface 221a may come into contact with a lower portion of the breast of the human when the breast is placed onto the first surface 221, while the second surface 221b may come into contact with a chest or stomach area below the breast of the human. The housing 221 may be formed of carbon-composite plastic.

The detector 220 may be positioned inside the housing 221 (e.g., internally). One surface positioned at an upper portion of the detector 220 may be parallel to the first surface 221a of the housing 221. If x-rays are radiated toward the first surface 221a from the x-ray generating unit 200, an internal image of the subject 4 may be obtained by the detector 220.

The thermoelectric element 40 may be positioned inside the housing 221 (e.g., internally). The thermoelectric element 40 may be positioned at a lower portion of the detector 220 while facing the detector 220. The thermoelectric element 40 may include the cooling unit 41 and the heat generating unit 42. The cooling unit 41 of the thermoelectric element 40 may be positioned in a way to face the other surface that is positioned at a lower portion of the detector 220. One surface of the cooling unit 41 of the thermoelectric element 40 may face the other surface of the detector 220, and the heat generating unit 42 may be provided at the other surface of the cooling unit 41.

The detector 220 may include a heat generating member configured to (suitable for, adapted to, capable of, arranged to, operable to, etc.) generate a large amount of heat. As the temperature of the detector 220 is increased, the x-ray photographing of the subject 4 may not be able to be obtained in an accurate manner. Thus, the detector 220 may be needed to be cooled so that the temperature of the detector 220 is not increased above a predetermined temperature. The detector 220 may be provided at an inside thereof, with a cooling system.

As the cooling unit 41 of the thermoelectric element 40 is positioned to face the other surface of the detector 220, the cooling of the detector 220 by the cooling unit 41 may be able to be performed. Even in a case when a cooling system is provided inside the detector 220, the cooling of the detector 220 may be additionally performed by the cooling unit 41. Through the above, the cooling effect of the detector 220 may be increased. The heat generated from the detector 220 may be cooled by the cooling unit 41. For example, the cooling of the detector 220 may be performed by a convection current of the air that is heated.

At this time, inside the housing 221, a blocking unit 224 configured to (suitable for, adapted to, capable of, arranged to, operable to, etc.) block the cooling unit 41 of the thermoelectric element 40 from the heat generating unit 42 may be provided. The blocking unit 224 may be manufactured with a material having low heat conductivity. Through the above, the heat generated from the heat generating unit 42 may not be delivered to the side of the cooling unit 41. The air that is heated by the detector 220 in a space that is formed by the detector 220 and the blocking unit 224 may be convectionally current, and may be cooled by the cooling unit 41 of the thermoelectric element 40. The air that is heated by the detector 220 may be discharged by a fan through an outlet (not shown) formed at one side of the x-ray detecting unit 22, and the air that is introduced through an inlet (not shown) may be cooled by the cooling unit 41 and may be supplied to the side of the detector 220.

The heat pipe 222 formed of metal having a high thermal conductivity may be connected to the heat generating unit 42. The heat pipe 222 may be formed of metal having a high thermal conductivity, such as copper or aluminum. The heat pipe 222 may extend from the heat generating unit 42 to the inner surface of the housing 221. Heat generated from the heat generation unit 42 may be delivered to the housing 221 by the heat pipe 222, to increase the temperature of the housing 221.

The heat pipe 222 may be extended along an edge of the housing 221. In detail, the heat pipe 222 may be extended along an inner edge of the first surface 221a and the second surface 221b of the housing 221. The heat generated from the heat generating unit 42 may be delivered to the first surface 221a and the second surface 221b, and a temperature of the first surface 221a and/or the second surface 221b may be increased. Through the above, the temperatures of the first surface 221a and the second surface 221b, which may make contact with a human body, are increased, and thus, the displeasure that is generated or experienced by the human at the time of an x-ray photographing may be minimized.

The housing 221 may be provided with a temperature detecting sensor 223. The temperature detecting sensor 223 may be provided at the side of the first surface 221a and/or at the side of the second surface 221b. The temperature detecting sensor 223, by detecting the temperature of the side of the first surface 221a and/or the side of the second surface 221b, may be able to deliver or transmit the temperature to a control unit (now shown). For example, the control unit (controller) may be embodied by the control unit 201 disposed in the body 2, and/or by a different control unit which may be disposed within the x-ray detecting unit 22 or connected thereto via a wired or wireless network or a combination thereof.

A range of temperatures to be maintained at the housing 221 may be predetermined at the control unit (not shown). That is, the range of temperatures may be stored at the control unit, for example in a memory or storage device. The control unit may be able to block the current that flows at the thermoelectric element 40 in a case when the temperature detected by the temperature detecting sensor 223 is greater than the predetermined temperature. That is, the control unit may compare the temperature measured or detected by the one or more temperature detecting sensors disposed at the housing 221, and the control unit may determine whether the temperature detected by the one or more temperature detecting sensor 223 is greater than the acceptable range of predetermined temperatures. As the current flowing at the thermoelectric element 40 is blocked, heat may no longer be generated from the heat generating unit 42. Thus, heat is no longer delivered to the housing 221 through the heat pipe 222. The control unit may be able to have current flow at the thermoelectric element 40 in a case when the temperature detected by the temperature detecting sensor 223 is smaller than the predetermined temperature. That is, the control unit (controller) may compare the temperature measured or detected by the one or more temperature detecting sensors disposed at the housing 221, and the control unit may determine whether the temperature detected by the one or more temperature detecting sensor 223 is less than the acceptable range of predetermined temperatures. As current flows again at the thermoelectric element 40, heat may be generated again from the heat generating unit 42, and the heat may be delivered through the heat pipe 222 to the housing 221. Based on the above operations of the control unit, the temperature of the housing 221 may be able to be maintained within the range of temperatures that is predetermined.

A heat insulating unit 228 may be further provided at the housing 221. The heat insulating unit 228 may be able to insulate the heat pipe 222 from other portions at an inside of the housing 221. The heat delivered through the heat pipe 222 may only then be used as to increase the temperature of the housing 221. Through the above, the heat of the heat pipe 222 may not be able to be delivered to other components at an inside the housing 221. Through the above, the heat of the heat pipe 222 may be prevented from being delivered to the side of the detector 220.

Figure 5:
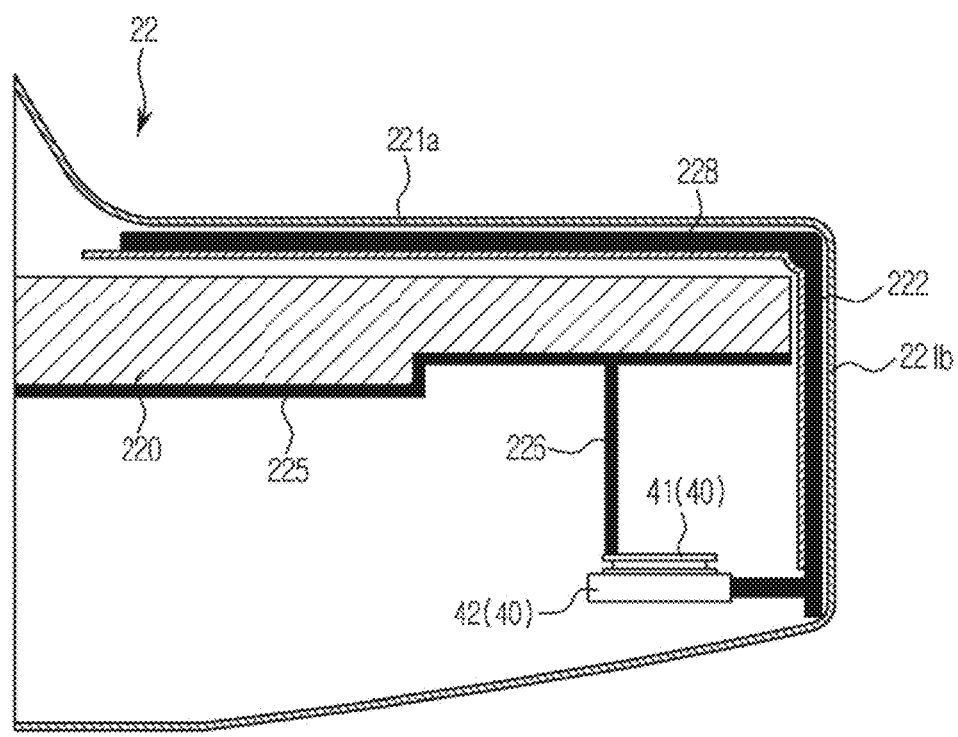
FIG. 5 is a cross-sectional view illustrating a portion of an x-ray detecting unit in accordance with an embodiment of the disclosure.

FIG. 5 is a cross-sectional view illustrating a portion of the x-ray detecting unit in accordance with an embodiment of the disclosure.

Referring to FIG. 5, the thermoelectric element 40 of the x-ray detecting unit 22 in accordance with an embodiment of the disclosure may be able to cool the detector 220 by thermal conduction. A thermal conductor 225 may be provided at the other surface of the detector 220. By way of example, the detector 220 may have a first surface which is adjacent to and faces the first surface 221a, while the other surface of the detector 220 may refer to a surface which is on an opposite side the detector 220. The thermal conductor 225 may be formed of a material having a high heat conductivity. The thermal conductor 225 provided at the other surface of the detector 220 may be connected to the cooling unit 41 of the thermoelectric element 40 by a heat pipe 226. As shown in FIG. 5, the thermal conductor 225 may extend from one side of the detector 220 to an opposite side of the detector 220 which is adjacent to the second surface 221b. The heat generated from the detector 220 may be delivered to the cooling unit 41 through the thermal conductor 225 and the heat pipe 226. Through the above, the detector 220 may be able to be cooled through thermal conduction.

A construction of delivering the heat generated from the heat generating unit 42 of the thermoelectric element 40 to the housing 221 through the heat pipe 222, as well as a construction of the temperature detecting sensor 223 and a heat insulating unit 228 may be implemented in a similar way as discussed above with respect to FIG. 4 of the disclosure. For example, when the detector 220 is cooled through heat conduction, the configuration or arrangement of the blocking unit 224 as shown in FIG. 4 of the disclosure may be omitted. However, in an alternative embodiment, a blocking unit may be provided in the x-ray detecting unit 22.

As discussed above, by having the cooling unit 41 of the thermoelectric element 40 connected to the thermal conductor 225 mounted at the other surface of the detector 220 such that the detector 220 is cooled by heat conduction, the cooling of the detector 220 may be efficiently performed. In addition, as the construction of the blocking unit 224 may be omitted, the space utilization of the x-ray detecting unit 22 may be efficiently performed.

Figure 6:
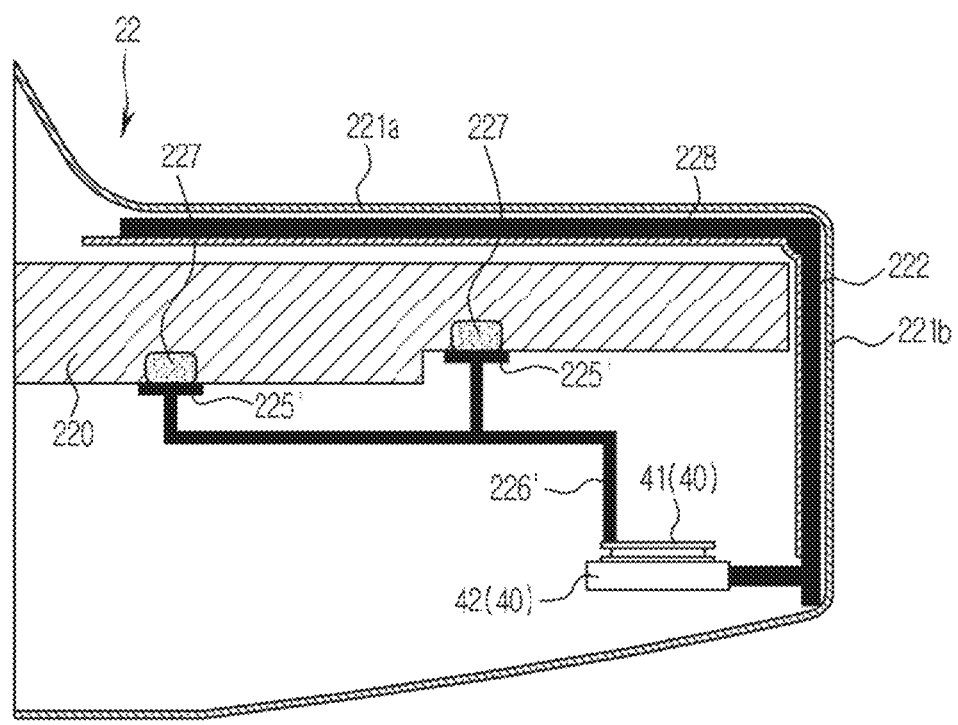
FIG. 6 is a cross-sectional view illustrating a portion of an x-ray detecting unit in accordance with an embodiment of the disclosure.

FIG. 6 is a cross-sectional view illustrating a portion of the x-ray detecting unit in accordance with an embodiment of the disclosure.

Referring to FIG. 6, the thermoelectric element 40 of the x-ray detecting unit 22 in accordance with an embodiment of the disclosure may be able to cool one or more heat generating members 227 of the detector 220 by heat conduction. One or more thermal conductors 225' may be provided at the other surface of the detector 220 at which the heat generating member 227 is positioned. The one or more thermal conductors 225' may only be provided at the side of the heat generating member 227. The one or more thermal conductors 225' may be connected to the cooling unit 41 of the thermoelectric element 40 by, for example, a heat pipe 226'. The heat that is generated from the one or more heat generating members 227 may be delivered to the cooling unit 41 through the one or more thermal conductors 225' and the heat pipe 226'. Through the above, the one or more heat generating members 227 may be cooled through heat conduction.

A construction of delivering the heat generated from the heat generating unit 42 of the thermoelectric element 40 to the housing 221 through the heat pipe 222, as well as a construction of the temperature detecting sensor 223 and a heat insulating unit 228 may be implemented in a similar way as discussed above with respect to FIG. 4 of the disclosure. For example, when the detector 220 is cooled through heat conduction, the configuration or arrangement of the blocking unit 224 as shown in FIG. 4 of the disclosure may be omitted. However, in an alternative embodiment, a blocking unit may be provided in the x-ray detecting unit 22.

As a portion of the other surface of the detector 220 at which the heat generating member 227 is positioned is selectively cooled, the cooling of the detector 220 may be able to be efficiently performed, and in addition, the space utilization of the space inside the x-ray detecting unit 22 may be efficiently performed, while the connections among the detector 220 and other components may be easily performed. In contrast to the x-ray detecting unit 22 as shown in FIG. 5, the one or more thermal conductors 225' as shown in FIG. 6 are disposed at selective portions of the detector 220 and do not extend from one side of the detector 220 across to an opposite side of the detector 220.

Based on the above, by use of the thermoelectric element 40, as the temperature of the housing 221 of the x-ray detecting unit 22 with which a human body may be in contact is increased and maintained in a warm manner, the displeasure that is generated by feeling the coldness when a portion of a human body is in contact with the x-ray detecting unit 22 may be minimized. As the housing 221 of the x-ray detecting unit 22 may be able to be maintained (automatically, e.g., using the control unit) in a way to have a constant range of temperatures at all times without an additional manipulation of an operator, a convenience may be provided for use. The temperature of the housing 221 may be increased by the single thermoelectric element 40, and at the same time, the detector 220 may be cooled.

The apparatuses and methods according to the above-described example embodiments may use one or more processors. For example, a processing device may be implemented using one or more general-purpose or special purpose computers, and may include, for example, one or more of a processor, a controller and an arithmetic logic unit, a central processing unit (CPU), a graphics processing unit (GPU), a digital signal processor (DSP), an image processor, a microcomputer, a field programmable array, a programmable logic unit, an application-specific integrated circuit (ASIC), a microprocessor or any other device capable of responding to and executing instructions in a defined manner.

Aspects of the apparatuses and methods according to the above-described embodiments may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as optical discs; and hardware devices that are specially configured to store and perform program instructions, such as read-only memory (ROM), random access memory (RAM), flash memory, USB memory, and the like. Examples of program instructions include both machine code, such as produced by a compiler, and files containing higher level code that may be executed by the computer using an interpreter. The program instructions may be executed by one or more processors. The described hardware devices may be configured to act as one or more software modules in order to perform the operations of the above-described embodiments, or vice versa. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

Although example embodiments of the disclosure have been shown and described, it would be appreciated by those skilled in the art that changes may be made to these embodiments without departing from the principles and spirit of the disclosure, the scope of which is defined in the claims and their equivalents.

What is claimed is:

1. A mammography apparatus, comprising:
an x-ray generating unit to generate x-rays;
an x-ray detecting unit including a housing forming an outer appearance of the x-ray detecting unit and a detector accommodated in the housing and configured to detect the x-rays that have passed through a subject;
a thermoelectric element provided in the housing and positioned at a lower portion of the detector, the thermoelectric unit including a cooling unit and a heat generating unit, the cooling unit disposed to face a lower surface of the detector to cool the detector, and the heat generating unit coupled to a lower surface of the cooling unit; and
a heat pipe extended from the heat generating unit to an upper portion of the detector in the housing, to increase a temperature of a surface of the housing being in contact with the subject.

2. The mammography apparatus of claim 1, wherein:
the heat pipe is extended along an edge of one surface of the housing, the one surface being in contact with or adjacent to a subject when a body part of the subject is disposed on a top surface of the housing.

3. The mammography apparatus of claim 1, wherein:
the x-ray detecting unit further comprises a heat insulating unit provided inside the housing to insulate the heat pipe from other portions of the x-ray detecting unit inside the housing.

4. The mammography apparatus of claim 1, wherein:
the x-ray detecting unit is provided with one or more temperature detecting sensors to detect the temperature of at least one surface of the housing.

5. The mammography apparatus of claim 4, wherein:
when the temperature detected by the one or more temperature detecting sensors is equal to or higher than a predetermined temperature, a current that flows at the thermoelectric element is blocked, and when the temperature detected by the one or more temperature detecting sensors is lower than the predetermined temperature, current flows at the thermoelectric element.

6. The mammography apparatus of claim 1, wherein:
the thermoelectric element is provided with a metallic material having high heat conductivity.

7. The mammography apparatus of claim 1, wherein:
a side of the cooling unit of the thermoelectric element is blocked from a side of the heat generating unit by a blocking unit.

8. The mammography apparatus of claim 1, wherein:
at least one thermal conductor is provided at a lower surface of the detector.

9. The mammography apparatus of claim 8, wherein:
the x-ray detecting unit further comprises a connecting heat pipe to connect the at least one thermal conductor to the cooling unit of the thermoelectric element.

10. The mammography apparatus of claim 8, wherein:
the at least one thermal conductor is provided at a side of a corresponding heat generating member provided at the detector.

11. A mammography apparatus, comprising:
an x-ray generating unit to radiate x-rays to a subject;
a detector configured to detect the x-rays that have passed through the subject;
a housing to accommodate the detector;
a thermoelectric element positioned at a lower portion of the detector inside the housing and including a heat generating unit and a cooling unit;
a heat pipe which extends from the heat generating unit to an upper portion of the detector inside the housing, to increase a temperature of a surface of the housing being in contact with the subject; and
one or more temperature detecting sensors to detect the temperature of the housing.

12. The mammography apparatus of claim 11, wherein:
the one or more temperature detecting sensors are provided on at least one surface of the housing.

13. The mammography apparatus of claim 11, wherein:
the housing further comprises a heat insulating unit to insulate the heat pipe.

14. The mammography apparatus of claim 11, wherein:
the housing further comprises a blocking unit to block a side of the cooling unit of the thermoelectric element from a side of the heat generating unit.

15. The mammography apparatus of claim 11, wherein:
at least one thermal conductor is provided at a lower surface of the detector.

16. The mammography apparatus of claim 15, wherein:
the housing further comprises a connecting heat pipe to connect the cooling unit of the thermoelectric element to the at least one thermal conductor.

17. The mammography apparatus of claim 15, wherein:
the at least one thermal conductor is provided at a surface of the detector on which a corresponding heat generating member is positioned.

18. A method of controlling a temperature of a housing of an x-ray detecting unit in a mammography apparatus, the method comprising:
radiating, using an x-ray generator, x-rays to a subject;
detecting, using a detector disposed in the housing, x-rays that have passed through the subject;
cooling the detector using a cooler disposed in the housing below the detector;
measuring, using one or more sensors, a temperature of the housing;
comparing the measured temperature with a prestored temperature range; and
controlling a heat generator disposed in the housing below the cooler, to selectively be turned on or off to control a temperature of the housing, based on the comparing, and
wherein the heat generator is connected to a heat pipe which extends from the heat generator to an upper portion of the detector inside the housing.

19. The method of claim 18, wherein:
when the comparing indicates the measured temperature exceeds the prestored temperature range, the controlling comprises turning off the heat generator, and
when the comparing indicates the measured temperature is less than the prestored temperature range, the controlling comprises turning on the heat generator.

20. The method of claim 19, wherein:
the one or more temperature detecting sensors are provided on at least one surface of the housing.

21. The method of claim 18, wherein:
the heat pipe further extends from the inner side surface of the housing to an inner top surface of the housing adjacent to a top surface of the housing upon which the subject is disposed.

* * * * *